US010385386B2

(12) United States Patent
Wu et al.

(10) Patent No.: US 10,385,386 B2
(45) Date of Patent: Aug. 20, 2019

(54) METHODS AND SYSTEMS FOR PCR QUANTITATION (71) Applicant: LIFE TECHNOLOGIES CORPORATION, Carlsbad, CA (US)

(72) Inventors: Yalei Wu, Foster City, CA (US); David Keys, Alameda, CA (US)

(73) Assignee: LIFE TECHNOLOGIES CORPORATION, Carlsbad, CA (US)

( * ) Notice: Subject to any disclaimer, the term of this patent is extended or adjusted under 35 U.S.C. 154(b) by 313 days.

(21) Appl. No.: 15/301,947

(22) PCT Filed: Apr. 3, 2015

(86) PCT No.: PCT/US2015/024249
§ 371 (c)(1),
(2) Date: Oct. 4, 2016

(87) PCT Pub. No.: WO2015/153973
PCT Pub. Date: Oct. 8, 2015

(65) Prior Publication Data
US 2018/0208979 A1    Jul. 26, 2018

Related U.S. Application Data

(60) Provisional application No. 61/975,614, filed on Apr. 4, 2014.

(51) Int. Cl.
*G16B 5/00* (2019.01)
*C12Q 1/6851* (2018.01)
(Continued)

(52) U.S. Cl.
CPC ............ *C12Q 1/6851* (2013.01); *G16B 5/00* (2019.02); *G16B 25/00* (2019.02); *G16B 30/00* (2019.02);
(Continued)

(58) Field of Classification Search
None
See application file for complete search history.

(56) References Cited

U.S. PATENT DOCUMENTS

| 6,355,435 B1 | 3/2002 | Wilson et al. |
| 2005/0089862 A1 | 4/2005 | Therianos et al. |

(Continued)

FOREIGN PATENT DOCUMENTS

EP    1138783    10/2001

OTHER PUBLICATIONS

Tuomi et al., Bias in the Cq value observed with hydrolysis probe based quantitative PCR can be corrected with the estimated PCR efficiency value, Methods. Apr. 2010;50(4):313-22. doi: 10.1016/j.ymeth.2010.02.003. Epub Feb. 6, 2010.*

(Continued)

*Primary Examiner* — Aaron A Priest
(74) *Attorney, Agent, or Firm* — François A. Pelaez (57) ABSTRACT

A method for quantifying nucleic acid is provided. The method includes determining a first reference threshold cycle for a first predetermined input quantity for a reference nucleic acid, determining a first target threshold cycle for the first predetermined input quantity for a target nucleic acid, determining a second reference threshold cycle for a second predetermined input quantity for the reference nucleic acid, and determining a second target threshold cycle, by the processor, for the second predetermined input quantity for the target nucleic acid. The method further includes receiving a sample threshold cycle, determining a sample input quantity based on the first and second reference threshold cycle and the first and second target threshold cycle, and displaying the sample input quantity to a user.

10 Claims, 13 Drawing Sheets

(51) Int. Cl.
  *G16B 30/00* (2019.01)
  *G16B 40/00* (2019.01)
  *G16B 45/00* (2019.01)
  *G16B 25/00* (2019.01)
  *C12Q 1/686* (2018.01)

(52) U.S. Cl.
  CPC ............. *G16B 40/00* (2019.02); *G16B 45/00* (2019.02); *C12Q 1/686* (2013.01); *C12Q 2537/16* (2013.01); *C12Q 2545/114* (2013.01)

(56) References Cited

U.S. PATENT DOCUMENTS

2012/0070840 A1 3/2012 Bechler et al.
2017/0177791 A1 6/2017 Wu et al.

OTHER PUBLICATIONS

PCT/US2015/024249, "International Search Report and Written Opinion", dated Sep. 9, 2015, 19 Pages.
Pfaffl, et al., "New Mathematical Model for Relative Quantification in Real-Time PCR", *Nucleic Acids Research*, vol. 29, No. 9, 2001, e45.
Pfaffl, et al., "Relative Expression Software Tool (REST) for Group-Wise Comparison and Statistical Analysis of Relative Expression Results in Real-Time PCR", *Nucleic Acids Research*, vol. 30, No. 9, May 1, 2002, 1-10.
Ramakers, C. et al., "Assumption-Free Analysis of Quantitative Real-Time Polymerase Chain Reaction (PCR) Data", *Neuroscience Letters*, vol. 339, 2003, 62-66.
Tuomi, J. M. et al., "Bias in the Cq Value Observed With Hydrolysis Probe Based Quantitative PCR Can be Corrected With the Estimated PCR Efficiency Value", *Methods*, vol. 50, 2010, 313-322.

* cited by examiner

METHODS AND SYSTEMS FOR PCR QUANTITATION

BACKGROUND

Quantitative nucleic acid analysis is extensively used in biological research and clinical analysis. Some of the applications which make use of this technology include: measurement of gene expression, monitoring of biological responses to stimuli, genomic-level gene quantitation, and pathogen detection. Typically, these methodologies utilize Polymerase Chain Reaction (PCR) as a means for selectively amplifying nucleic acid sequences in a manner that allows for their detection. While it is generally desirable to automate the quantitation process, conventional methodologies often require a degree of user input in the form of subjective interpretation and/or approximation. As a result, these techniques may suffer from reduced accuracy and significant user-induced variability. Furthermore, in high-throughput applications where many samples are to be processed simultaneously, it is desirable to provide increased automation capabilities to improve the speed with which the analysis may be conducted. The aforementioned limitations of conventional techniques illustrate the need for an improved method for analyzing data generated by PCR-based quantitation techniques that may increase the potential for automation while improving the quantitative accuracy and reproducibility of the analysis.

SUMMARY

In one exemplary embodiment, a method for quantifying nucleic acid is provided. The method includes determining a first reference threshold cycle for a first predetermined input quantity for a reference nucleic acid, determining a first target threshold cycle for the first predetermined input quantity for a target nucleic acid, determining a second reference threshold cycle for a second predetermined input quantity for the reference nucleic acid, and determining a second target threshold cycle, by the processor, for the second predetermined input quantity for the target nucleic acid. The method further includes receiving a sample threshold cycle, determining a sample input quantity based on the first and second reference threshold cycle and the first and second target threshold cycle, and displaying the sample input quantity to a user.

DETAILED DESCRIPTION

To provide a more thorough understanding of the present invention, the following description sets forth numerous specific details, such as specific configurations, parameters, examples, and the like. It should be recognized, however, that such description is not intended as a limitation on the scope of the present invention, but is intended to provide a better description of the exemplary embodiments.

Various embodiments described herein generally relate to nucleic acid analysis, and more particularly, to a system and methods for evaluating results obtained from quantitative amplification reactions.

Those skilled in the art will recognize that the operations of the various embodiments may be implemented using hardware, software, firmware, or combinations thereof, as appropriate. For example, some processes can be carried out using processors or other digital circuitry under the control of software, firmware, or hard-wired logic. (The term "logic" herein refers to fixed hardware, programmable logic and/or an appropriate combination thereof, as would be recognized by one skilled in the art to carry out the recited functions.) Software and firmware can be stored on computer-readable media. Some other processes can be implemented using analog circuitry, as is well known to one of ordinary skill in the art. Additionally, memory or other storage, as well as communication components, may be employed in embodiments of the invention.

Figure 1:
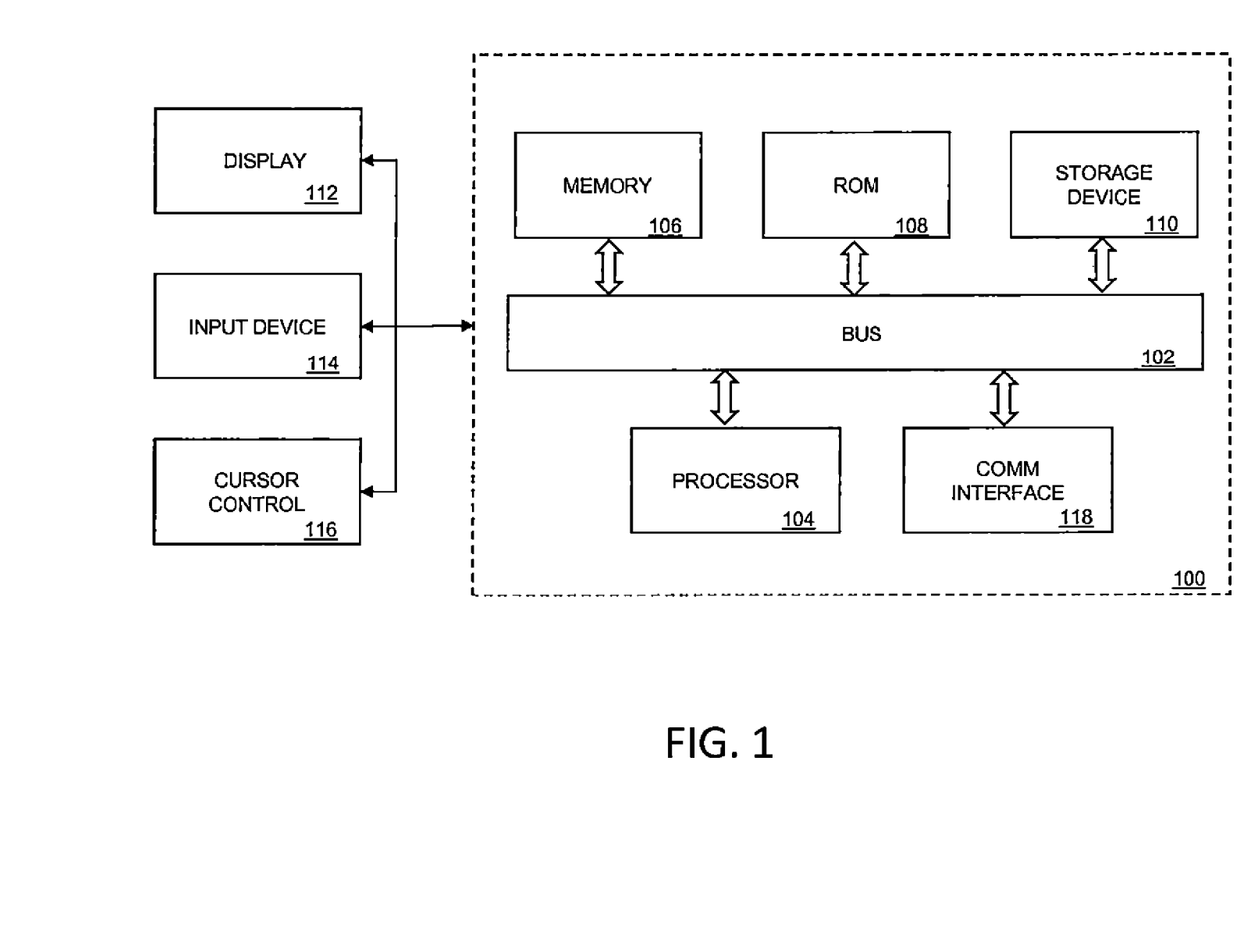
FIG. 1 illustrates an exemplary block diagram of a computing system for implementing the quantitation method according to various embodiments described herein.

FIG. 1 is a block diagram that illustrates a computer system 100 that may be employed to carry out processing functionality, according to various embodiments, upon which embodiments of a thermal cycler system (not shown) may utilize. Computing system 100 can include one or more processors, such as a processor 104. Processor 104 can be implemented using a general or special purpose processing engine such as, for example, a microprocessor, controller or other control logic. In this example, processor 104 is connected to a bus 102 or other communication medium.

Further, it should be appreciated that a computing system 100 of FIG. 1 may be embodied in any of a number of forms, such as a rack-mounted computer, mainframe, supercomputer, server, client, a desktop computer, a laptop computer, a tablet computer, hand-held computing device (e.g., PDA, cell phone, smart phone, palmtop, etc.), cluster grid, netbook, embedded systems, or any other type of special or general purpose computing device as may be desirable or appropriate for a given application or environment. Additionally, a computing system 100 can include a conventional network system including a client/server environment and one or more database servers, or integration with LIS/LIMS infrastructure. A number of conventional network systems, including a local area network (LAN) or a wide area network (WAN), and including wireless and/or wired components, are known in the art. Additionally, client/server environments, database servers, and networks are well documented in the art.

Computing system 100 may include bus 102 or other communication mechanism for communicating information, and processor 104 coupled with bus 102 for processing information.

Computing system 100 also includes a memory 106, which can be a random access memory (RAM) or other dynamic memory, coupled to bus 102 for storing instructions to be executed by processor 104. Memory 106 also may be used for storing temporary variables or other intermediate information during execution of instructions to be executed by processor 104. Computing system 100 further includes a read only memory (ROM) 108 or other static storage device coupled to bus 102 for storing static information and instructions for processor 104.

Computing system 100 may also include a storage device 110, such as a magnetic disk, optical disk, or solid state drive (SSD) is provided and coupled to bus 102 for storing information and instructions. Storage device 110 may include a media drive and a removable storage interface. A media drive may include a drive or other mechanism to support fixed or removable storage media, such as a hard disk drive, a floppy disk drive, a magnetic tape drive, an optical disk drive, a CD or DVD drive (R or RW), flash drive, or other removable or fixed media drive. As these examples illustrate, the storage media may include a computer-readable storage medium having stored therein particular computer software, instructions, or data.

In alternative embodiments, storage device 110 may include other similar instrumentalities for allowing computer programs or other instructions or data to be loaded into computing system 100. Such instrumentalities may include, for example, a removable storage unit and an interface, such as a program cartridge and cartridge interface, a removable memory (for example, a flash memory or other removable memory module) and memory slot, and other removable storage units and interfaces that allow software and data to be transferred from the storage device 110 to computing system 100.

Computing system 100 can also include a communications interface 118. Communications interface 118 can be used to allow software and data to be transferred between computing system 100 and external devices. Examples of communications interface 118 can include a modem, a network interface (such as an Ethernet or other NIC card), a communications port (such as for example, a USB port, a RS-232C serial port), a PCMCIA slot and card, Bluetooth, etc. Software and data transferred via communications interface 118 are in the form of signals which can be electronic, electromagnetic, optical or other signals capable of being received by communications interface 118. These signals may be transmitted and received by communications interface 118 via a channel such as a wireless medium, wire or cable, fiber optics, or other communications medium. Some examples of a channel include a phone line, a cellular phone link, an RF link, a network interface, a local or wide area network, and other communications channels.

Computing system 100 may be coupled via bus 102 to a display 112, such as a cathode ray tube (CRT) or liquid crystal display (LCD), for displaying information to a computer user. An input device 114, including alphanumeric and other keys, is coupled to bus 102 for communicating information and command selections to processor 104, for example. An input device may also be a display, such as an LCD display, configured with touchscreen input capabilities. Another type of user input device is cursor control 116, such as a mouse, a trackball or cursor direction keys for communicating direction information and command selections to processor 104 and for controlling cursor movement on display 112. This input device typically has two degrees of freedom in two axes, a first axis (e.g., x) and a second axis (e.g., y), that allows the device to specify positions in a plane. A computing system 100 provides data processing and provides a level of confidence for such data. Consistent with certain implementations of embodiments of the present teachings, data processing and confidence values are provided by computing system 100 in response to processor 104 executing one or more sequences of one or more instructions contained in memory 106. Such instructions may be read into memory 106 from another computer-readable medium, such as storage device 110. Execution of the sequences of instructions contained in memory 106 causes processor 104 to perform the process states described herein. Alternatively hard-wired circuitry may be used in place of or in combination with software instructions to implement embodiments of the present teachings. Thus implementations of embodiments of the present teachings are not limited to any specific combination of hardware circuitry and software.

The term "computer-readable medium" and "computer program product" as used herein generally refers to any media that is involved in providing one or more sequences or one or more instructions to processor 104 for execution. Such instructions, generally referred to as "computer program code" (which may be grouped in the form of computer programs or other groupings), when executed, enable the computing system 100 to perform features or functions of embodiments of the present invention. These and other forms of computer-readable media may take many forms, including but not limited to, non-volatile media, volatile media, and transmission media. Non-volatile media includes, for example, solid state, optical or magnetic disks, such as storage device 110. Volatile media includes dynamic memory, such as memory 106. Transmission media includes coaxial cables, copper wire, and fiber optics, including the wires that comprise bus 102.

Common forms of computer-readable media include, for example, a floppy disk, a flexible disk, hard disk, magnetic tape, or any other magnetic medium, a CD-ROM, any other optical medium, punch cards, paper tape, any other physical medium with patterns of holes, a RAM, PROM, and EPROM, a FLASH-EPROM, any other memory chip or cartridge, a carrier wave as described hereinafter, or any other medium from which a computer can read.

Various forms of computer readable media may be involved in carrying one or more sequences of one or more instructions to processor 104 for execution. For example, the instructions may initially be carried on magnetic disk of a remote computer. The remote computer can load the instructions into its dynamic memory and send the instructions over a telephone line using a modem. A modem local to computing system 100 can receive the data on the telephone line and use an infra-red transmitter to convert the data to an infra-red signal. An infra-red detector coupled to bus 102 can receive the data carried in the infra-red signal and place the data on bus 102. Bus 102 carries the data to memory 106, from which processor 104 retrieves and executes the instructions. The instructions received by memory 106 may optionally be stored on storage device 110 either before or after execution by processor 104.

It will be appreciated that, for clarity purposes, the above description has described embodiments of the invention with reference to different functional units and processors. However, it will be apparent that any suitable distribution of functionality between different functional units, processors or domains may be used without detracting from the invention. For example, functionality illustrated to be performed by separate processors or controllers may be performed by the same processor or controller. Hence, references to specific functional units are only to be seen as references to suitable means for providing the described functionality, rather than indicative of a strict logical or physical structure or organization.

In various embodiments, the devices, instruments, systems, and methods described herein may be used to detect one or more types of biological components of interest. These biological components of interest may be any suitable biological target including, but are not limited to, DNA sequences (including cell-free DNA), RNA sequences, genes, oligonucleotides, molecules, proteins, biomarkers, cells (e.g., circulating tumor cells), or any other suitable target biomolecule.

In various embodiments, such biological components may be used in conjunction with various PCR, qPCR, and/or dPCR methods and systems in applications such as fetal diagnostics, multiplex dPCR, viral detection and quantification standards, genotyping, sequencing validation, mutation detection, detection of genetically modified organisms, rare allele detection, and copy number variation. Embodiments of the present disclosure are generally directed to devices, instruments, systems, and methods for monitoring or measuring a biological reaction for a large number of small volume samples. As used herein, samples may be referred to as sample volumes, or reactions volumes, for example.

While generally applicable to quantitative polymerase chain reactions (qPCR) where a large number of samples are being processed, it should be recognized that any suitable PCR method may be used in accordance with various embodiments described herein. Suitable PCR methods include, but are not limited to, digital PCR, allele-specific PCR, asymmetric PCR, ligation-mediated PCR, multiplex PCR, nested PCR, qPCR, genome walking, and bridge PCR, for example.

As described below, in accordance with various embodiments described herein, reaction sites may include, but are not limited to, through-holes, wells, indentations, spots, cavities, sample retainment regions, and reaction chambers, for example.

Furthermore, as used herein, thermal cycling may include using a thermal cycler, isothermal amplification, thermal convention, infrared mediated thermal cycling, or helicase dependent amplification, for example. In some embodiments, the chip may be integrated with a built-in heating element. In various embodiments, the chip may be integrated with semiconductors.

In various embodiments, the devices, instruments, systems, and methods described herein may be used to detect one or more types of biological components of interest. These biological components of interest may include, but are not limited to, DNA sequences, RNA sequences, genes, oligonucleotides, or cells (e.g., circulating tumor cells). In various embodiments, such biological components may be used in conjunction with various PCR, qPCR, and/or dPCR methods and systems in applications such as fetal diagnostics, viral detection and quantification standards, genotyping, sequencing validation, mutation detection, detection of genetically modified organisms, rare allele detection, and copy number variation.

TaqMan® Mutation Detection Assays can be used to determine the mutation status for a given sample by running mutant allele assays paired with a corresponding gene reference assay.

According to various embodiments described herein, to get the quantitation information about mutants, each sample is tested with two different assays, such as mutant assay for the mutation of interests, and a reference assay which will cover both the wild-type and mutant allele.

Figure 2A:
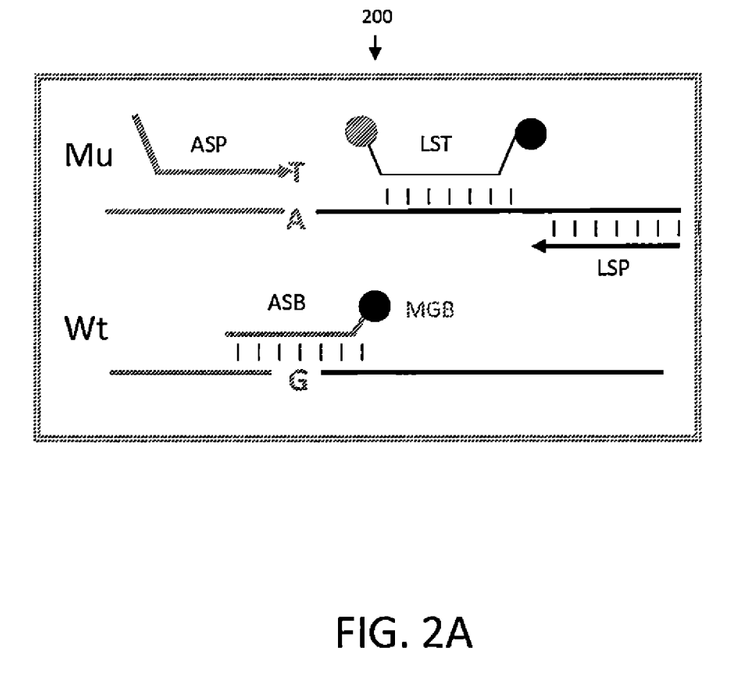
FIG. 2A illustrates an example of a mutant allele assay according to various embodiments described herein.

FIG. 2A illustrates an exemplary mutant allele assay 200. The mutant allele assay is designed to mutations in the COSMIC db to detect specific or multiple alleles. More specifically, an allele-specific primer detects the mutant allele, while an MGB oligonucleotide blocker suppresses the wild type allele. The assay name may be Gene symbol_COSMIC ID_mu, e.g. KRAS_517_mu.

It should be recognized that corresponding wild type allele assays are available for only a subset of the mutations. These can be paired with their corresponding mutant allele assays.

Figure 2B:
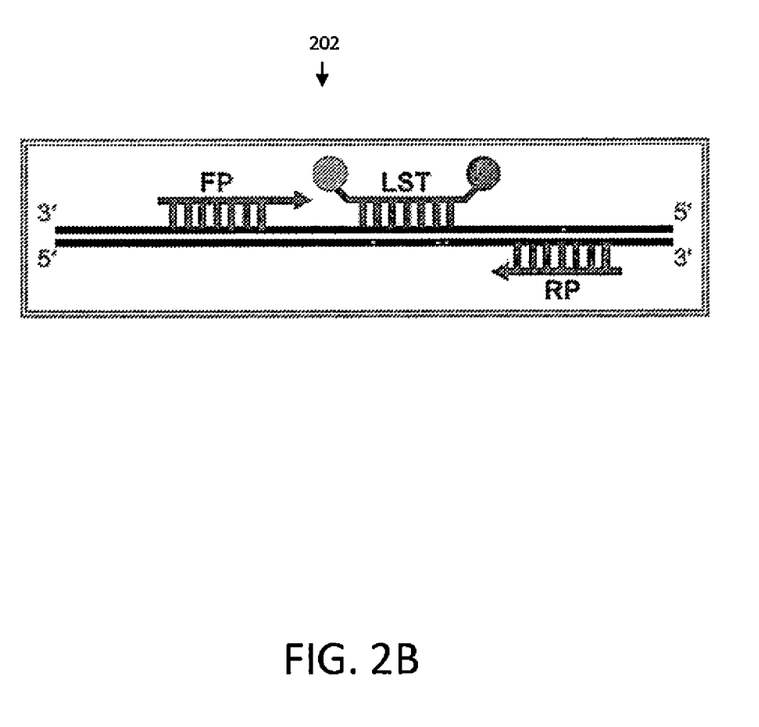
FIG. 2B illustrates an example of a gene reference assay according to various embodiments described herein.

FIG. 2B illustrates an example of a gene reference assay 202. Gene reference assay 202 detects a gene that target mutations reside in. Here, a locus-specific primer pair amplify a mutation-free region of the target gene. The assay name may be: Gene symbol_rf, e.g. KRAS_rf.

There is often a high amount of wild-type background template. To remedy this situation, the mutant assay is often pushed to its limit for high specificity and additional component is employed, of which the characteristics of PCR performance are no longer typical. As a result, the PCR efficiency is often below 100% leading to delays in Ct. According to the method described herein, Ct data of the mutant ($Ct_{mu}$) and Ct data from the reference ($Ct_{ref}$) are used. In this way, presence/absence information and percentage of mutation are results are obtained.

The previously-used delta Ct method accounts for delayed Ct values, but not the efficiency difference.

Figure 3A:
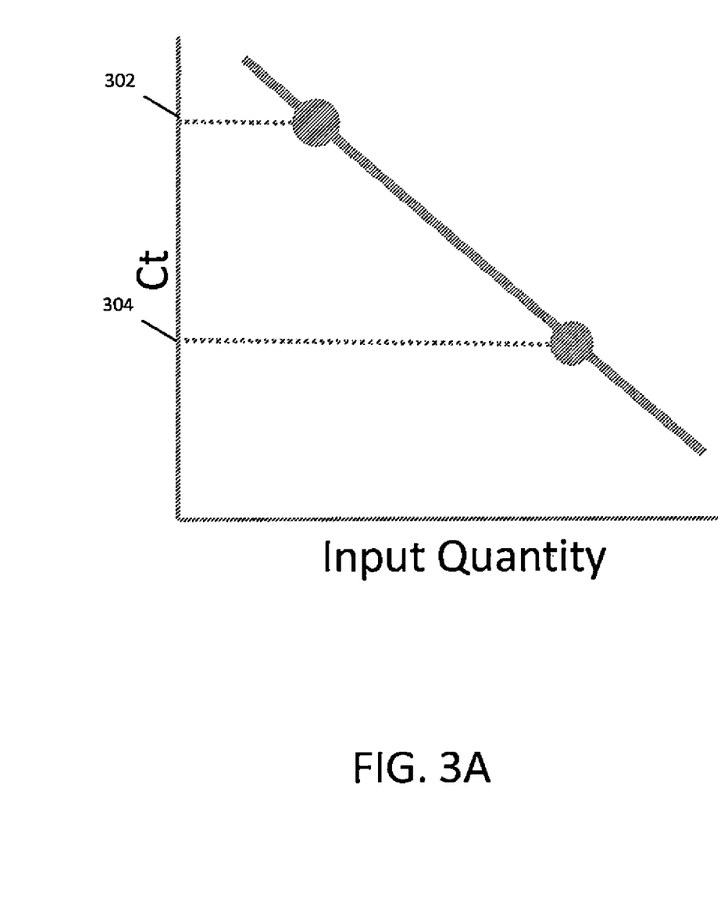
FIG. 3A illustrates a plot of Ct versus input quantity according to various embodiments described herein.

FIG. 3A illustrates an example plot of Ct versus input quantity where the gene reference assay and the mutant detection have the same efficiency and sensitivity. Here, $Ct_{mu}$ 302 can be directly compared to $Ct_{rf}$ 304.

Figure 3B:
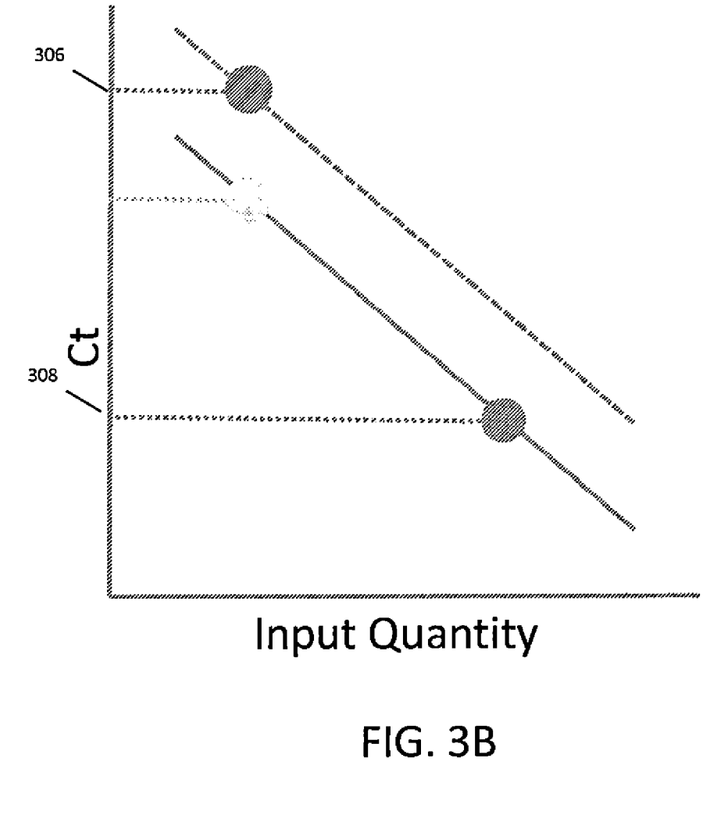
FIG. 3B illustrates a plot of Ct versus input quantity according to various embodiments described herein.

FIG. 3B illustrates an example plot of Ct versus input quantity. In this example, as opposed to the example in FIG. 3A, the efficiencies are the same, but sensitivities are different. In this example, the $Ct_{rf}$ 308 was much earlier than the $Ct_{mu}$ 306 and corresponds to a higher input quantity. According to embodiments described herein, the mutation percentage of the sample may be calculated by the following equation:

$$\text{Mutation \%} = 2^{-(Ct_{mu}-Ct_{rf})}$$

Figure 4:
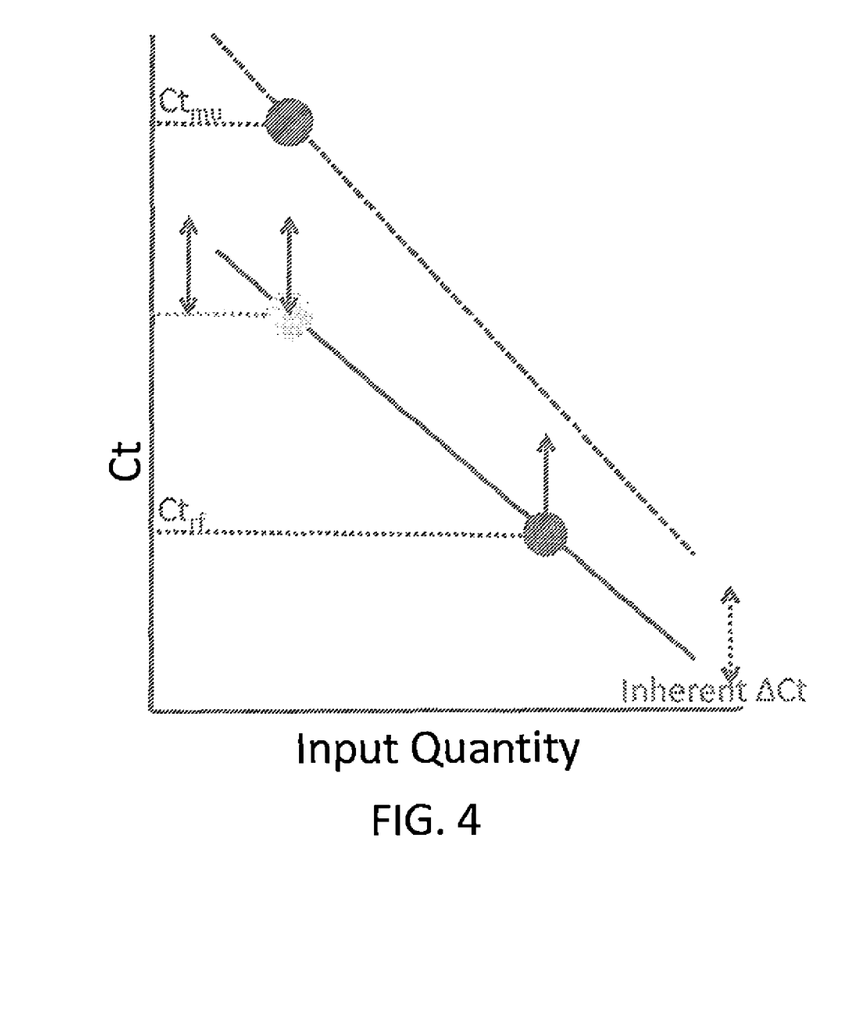
FIG. 4 illustrates another plot of Ct versus input quantity according to various embodiments described herein.

FIG. 4 illustrates another example plot of Ct versus input quantity. In this example, the both the efficiencies and sensitivities are different. This is the typical scenario for mutant assays. The previously-used delta Ct method would not work with assays such as the ones used in FIG. 4.

Generally, according to embodiments described herein, each sample will be run with two different assays: one is mutant specific, the other is for gene specific which will be used as denominator for percentage calculation.

The existing quantitation method relies on a pre-calculated value that's provided by us, inherent $\Delta Ct$. The purpose is to control the difference between the two different assays. It is generated with a fixed amount of template for each assay.

$$\text{Mutant percentage} = 0.5^{((Ct_{mu}-Ct_{rf})-\Delta Ct_{inherent})} * 100\%$$

The inherent $\Delta Ct$ is effective to capture one aspect of the differences between the two assays. Briefly, the existing method is not effective for sample and assay combination away from the condition that inherent ΔCt was generated, such as sample amount and the PCR efficiencies away from the expected 100%.

Figure 5:
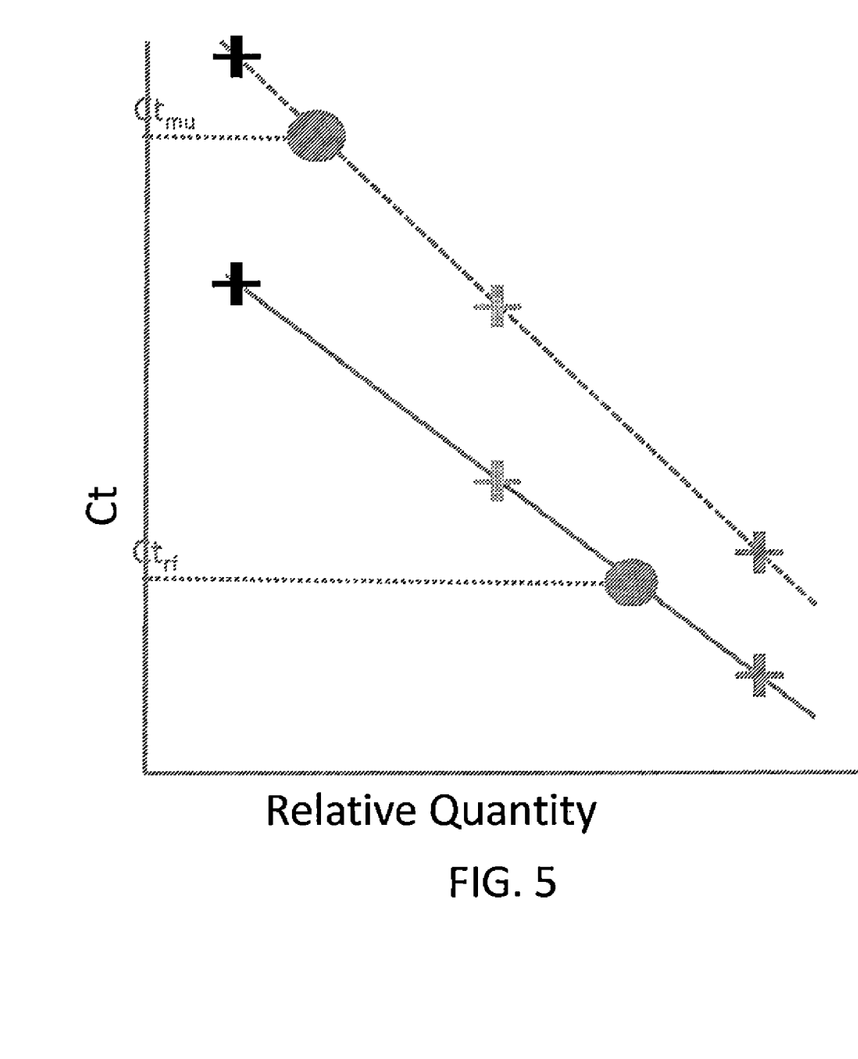
FIG. 5 illustrates Ct versus relative quantity according to various embodiments described herein.

According to other embodiments of the present teachings, a quantitation curve may be generated. FIG. 5 illustrates a plot of Ct versus relative quantity. Mutant percentage is a type of relative quantitation. By running a series of dilutions of a calibrator, with known ratio between mutant and reference assay target, a ratio of unknown sample can be deduced. This is because the initial concentration of the calibrator is no longer relevant.

Figure 6:
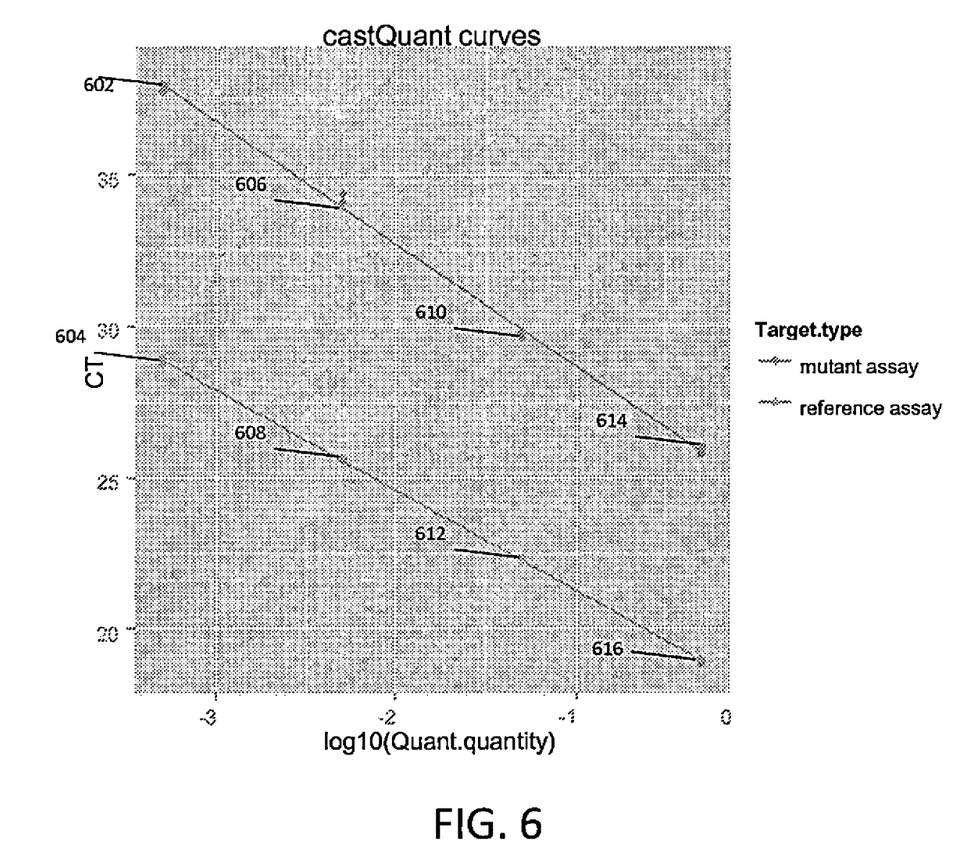
FIG. 6 illustrates a quantitation curve according various embodiments described herein.

FIG. 6 illustrates a quantitation curve according various embodiments described herein. FIG. 6 illustrates a plot of the Ct and the dilution ratio (in log 10). $Ct_{mu}$s 602, 606, 610, and 614 are plotted for dilutions of 0.001×, 0.01×, 0.1×, and 1×, respectively. Similarly, $Ct_{rf}$s 604, 608, 612, and 616 are plotted for dilutions of 0.001×, 0.01×, 0.1×, and 1×, respectively. As such, the curves illustrated in FIG. 6 may be used to determine a quantity of an unknown sample.

Figure 7:
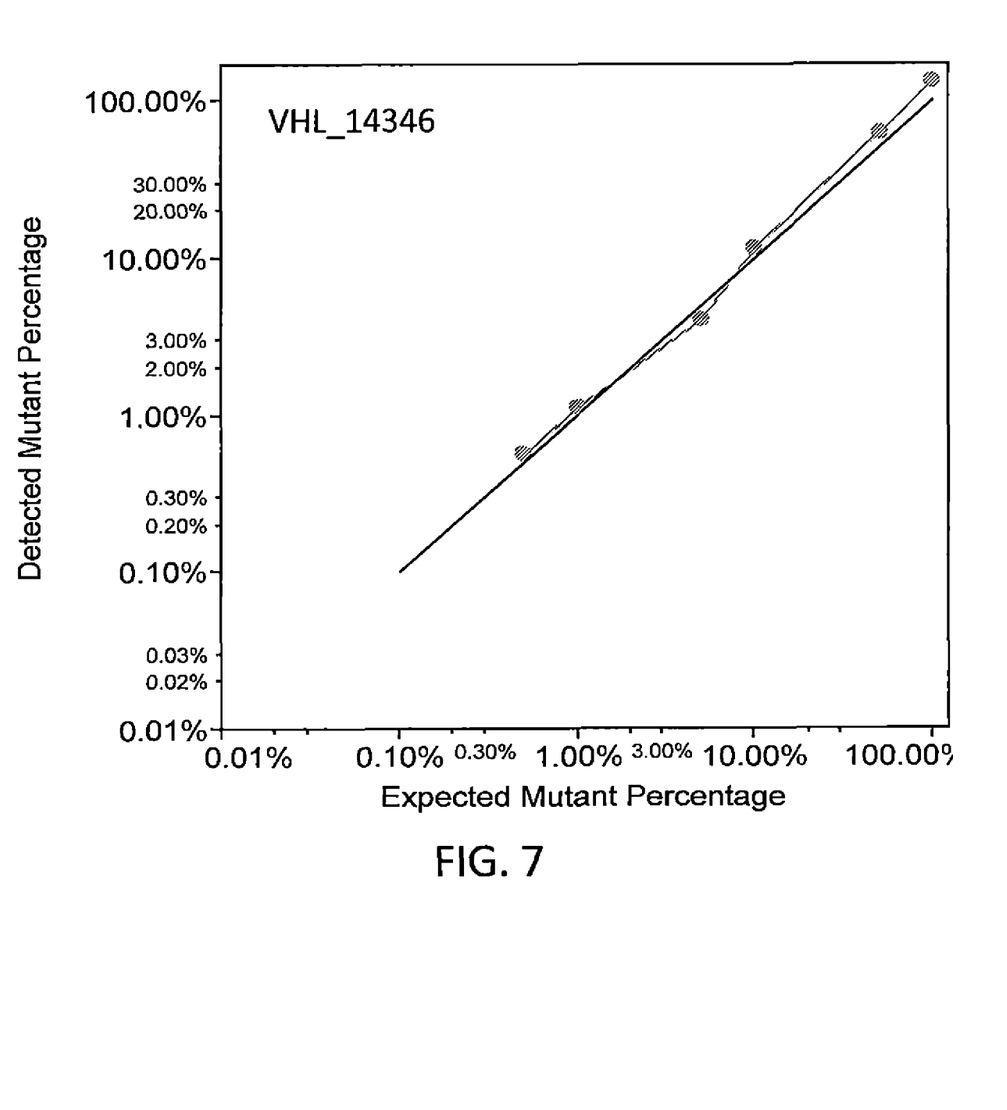
FIG. 7 illustrates data to support the performance of the quantitation method according to various embodiments described herein.

FIG. 7 illustrates data to support the performance of the quantitation method according to various embodiments described herein.

Figure 8A:
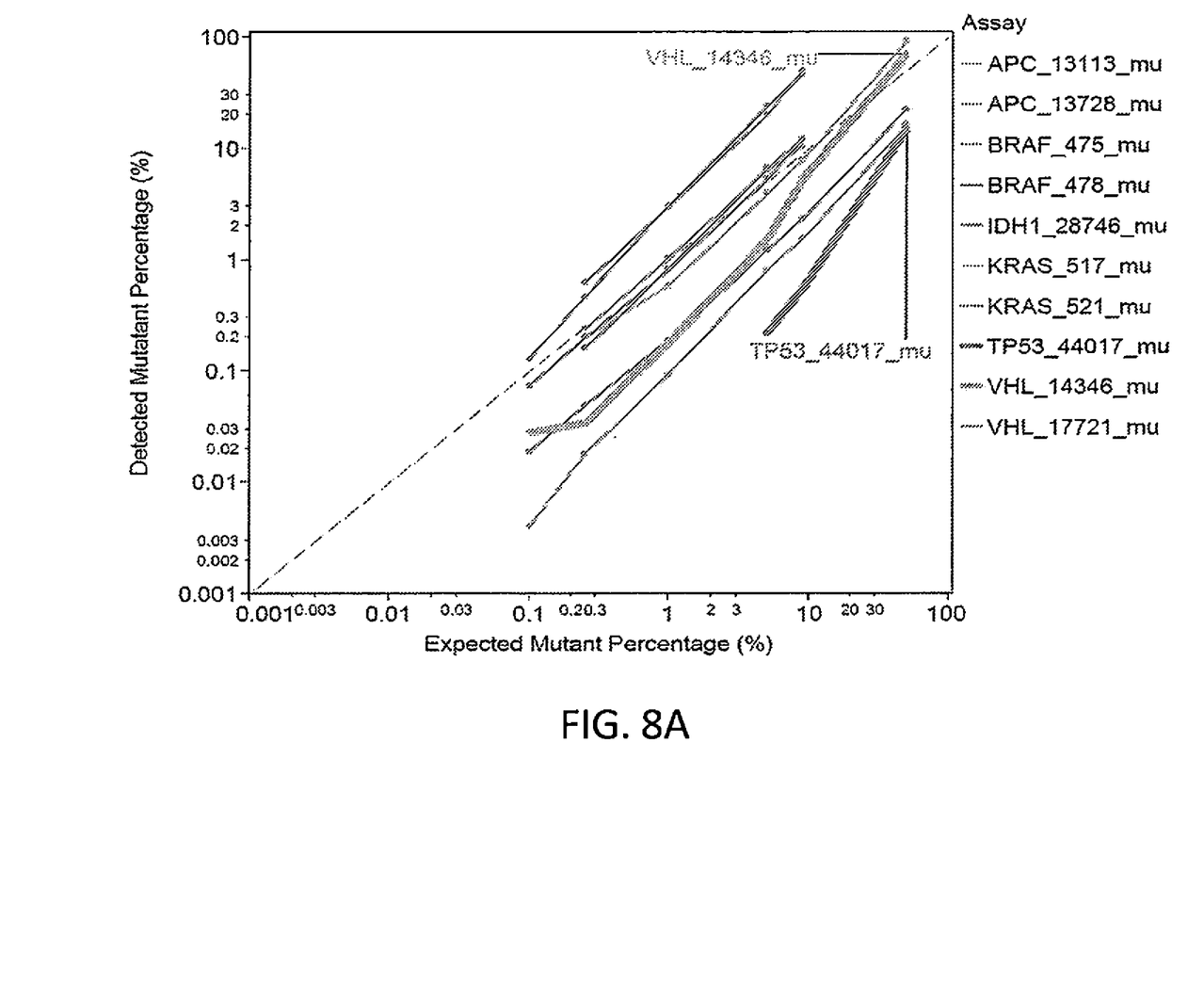
FIG. 8A and FIG. 8B illustrate several assays of the Von Hippel-Lindau tumor suppressor, an E3 ubiquitin protein ligase according to various embodiments described herein.
Figure 8B:
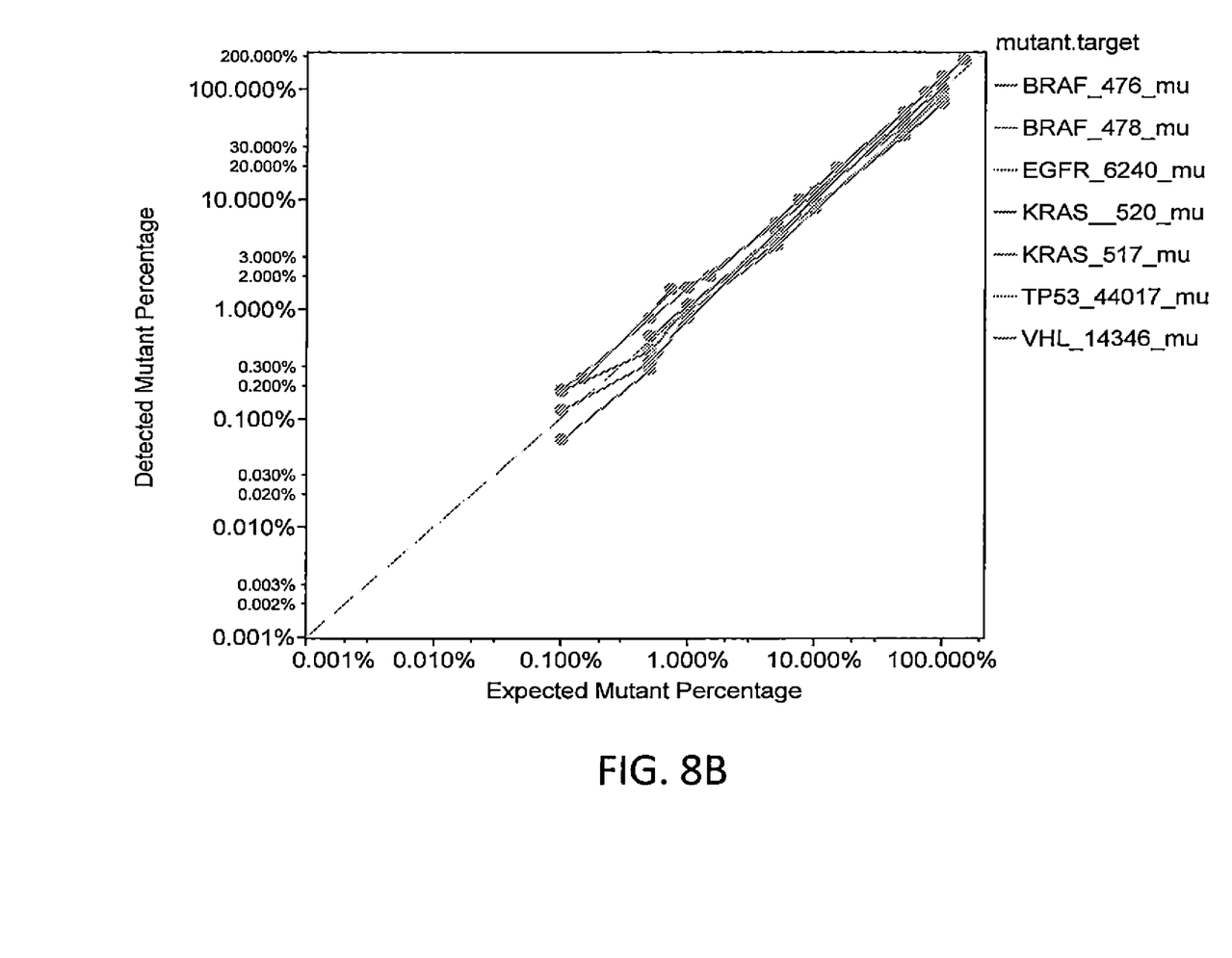

FIG. 8A and FIG. 8B illustrate several assays of the Von Hippel-Lindau tumor suppressor, an E3 ubiquitin protein ligase. FIG. 8A illustrates a plot of detected mutant percentage versus an expected mutant percentage using commonly used methods. On the other hand, FIG. 8B illustrates a plot of detected mutant percentage versus an expected mutant percentage according to various embodiments described herein. Independent of the assays, it is seen that the method according to embodiments of the present teachings lead to closer detected mutant percentages with respect to the expected mutant percentages (FIG. 8B) as compared with detected mutant percentages determined by the delta Ct method versus the expected mutant percentages (FIG. 8A).

Figure 9A:
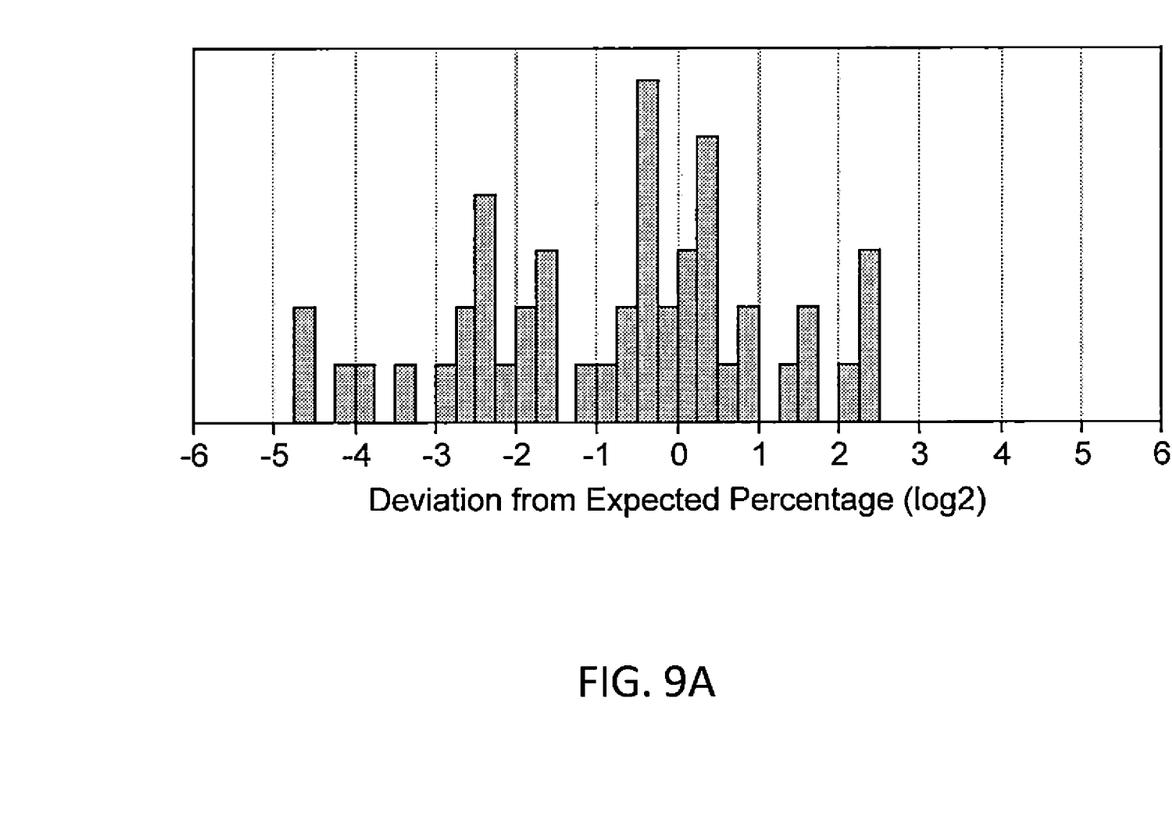
FIG. 9A and FIG. 9B illustrate the deviation of expected mutant percentage compared with the expected mutant percentage according to various embodiments described herein.
Figure 9B:
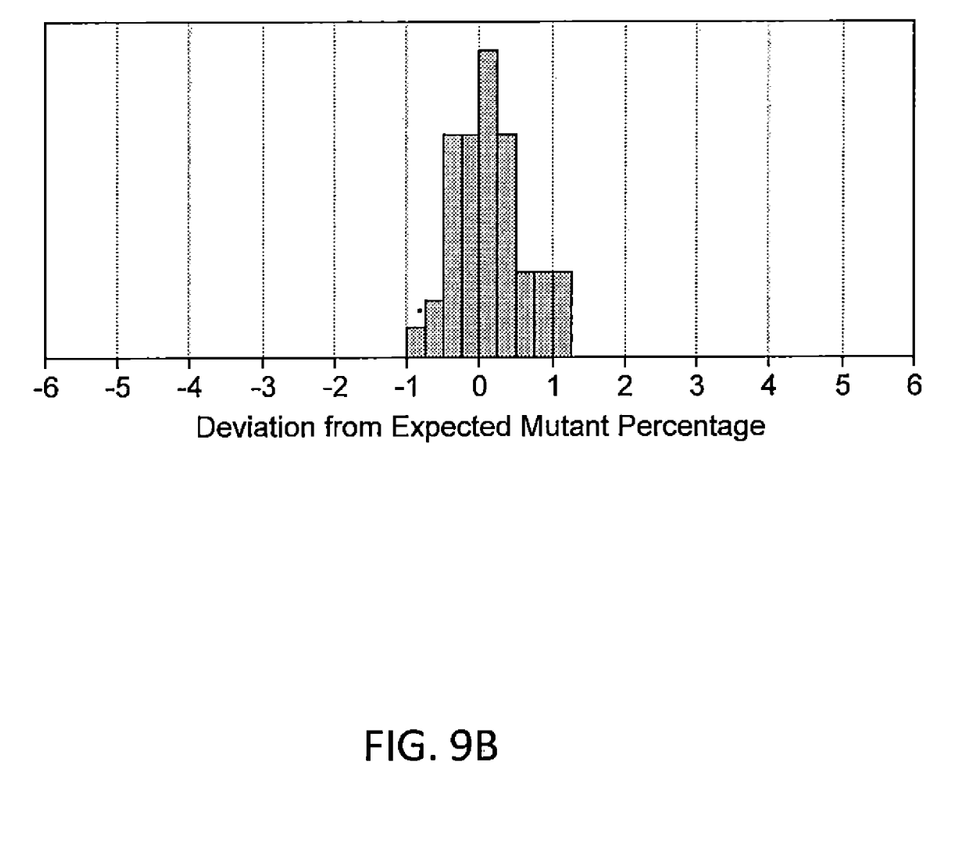

Similarly, FIGS. 9A and 9B illustrate an improvement of accuracy using the method according to embodiments described herein versus the delta Ct method. Both FIG. 9A and FIG. 9B illustrate the deviation of expected mutant percentage compared with the expected mutant percentage. FIG. 9A illustrates the deviation from expected mutation percentage using mutation percentages determined by the delta Ct method. On the other hand, FIG. 9B illustrates the deviation from expected mutant percentage from mutation percentages determined by methods according to embodiments of the present teachings. The deviation is much less using the method of the present teachings (FIG. 9B) compared with the deviation using the delta Ct method (FIG. 9A)

Although the present invention has been described with respect to certain exemplary embodiments, examples, and applications, it will be apparent to those skilled in the art that various modifications and changes may be made without departing from the invention.

What is claimed is:

1. A method for quantifying a sample mutant nucleic acid, the method comprising:
   determining a first reference threshold cycle for a first predetermined input quantity for a reference nucleic acid;
   determining a first target threshold cycle for a first predetermined input quantity for a mutant nucleic acid;
   determining a second reference threshold cycle for a second predetermined input quantity for the reference nucleic acid;
   determining a second target threshold cycle for a second predetermined input quantity for the mutant nucleic acid;
   calculating an inherent delta Ct between the threshold cycles of the first and second reference threshold cycles and the first and second target threshold cycles;
   receiving a sample threshold cycle;
   determining a mutant percentage of the sample based on the first and second reference threshold cycles and the first and second mutant threshold cycles, the inherent delta Ct and the sample threshold cycle using the equation:

$$\text{Mutant percentage}=0.5^{((Ct_{mu}-Ct_{rf})-\Delta Ct_{inherent})}*100\%;$$

and
   displaying the mutant percentage to a user.

2. The method of claim 1, wherein the first and second reference thresholds are determined by a gene reference assay.

3. The method of claim 1, wherein the sample input quantity is calculated with the following equation:

$$\text{sample input quantity }\%=2^{-(ct_{mu}-ct_{rf})}.$$

4. The method of claim 2, wherein the sensitivities of the mutation detection assay and the gene reference assay are different.

5. The method of claim 2, wherein the efficiencies of the mutation detection assay and the gene reference assay are different.

6. A system for quantifying a nucleic acid, the system comprising:
   a threshold cycle determination processor comprising program code comprising instructions, which when executed cause the processor to:
   determine a first reference threshold cycle for a first predetermined input quantity for a reference nucleic acid,
   determine a first target threshold cycle for a first predetermined input quantity for a mutant nucleic acid,
   determine a second reference threshold cycle for a second predetermined input quantity for the reference nucleic acid, and
   determine a second target threshold cycle for a second predetermined input quantity for the mutant nucleic acid;
   a quantity determination processor comprising program code comprising instructions, which when executed cause the processor to:
   calculate an inherent delta Ct between the threshold cycles of the first and second reference threshold cycles and the first and second target threshold cycles;
   receive a sample threshold cycle,
   determine a mutant percentage of the sample based on the first and second reference threshold cycles and the first and second mutant threshold cycles, the inherent delta Ct and the sample threshold cycle using the equation:

$$\text{Mutant percentage}=0.5^{((Ct_{mu}-Ct_{rf})-\Delta Ct_{inherent})}*100\%;$$

and
   a display screen configured to display the mutant percentage to a user.

7. The system of claim 6, wherein the first and second reference thresholds are determined by a gene reference assay.

8. The system of claim 6, wherein the sample input quantity is calculated with the following equation:

$$\text{sample input quantity }\%=2^{-(ct_{mu}-ct_{rf})}.$$

9. The system of claim 7, wherein the sensitivities of the mutation detection assay and the gene reference assay are different.

10. The system of claim 7, wherein the efficiencies of the mutation detection assay and the gene reference assay are different.

* * * * *